United States Patent [19]

Pols

[11] 4,265,033
[45] May 5, 1981

[54] SHOE TO BE WORN OVER CAST

[76] Inventor: Sidney R. Pols, c/o E. J. Sabel & Co., Benson East Bldg., P.O. Box 644, Jenkintown, Pa. 19046

[21] Appl. No.: 22,447

[22] Filed: Mar. 21, 1979

[51] Int. Cl.³ .......................... A43B 7/00; A43B 7/14
[52] U.S. Cl. ........................................ 36/110; 36/37; 36/69; 36/81; 128/83.5
[58] Field of Search ................ 36/110, 1, 8.1, 37, 36/69, 81; 128/82, 83.5

[56] References Cited

U.S. PATENT DOCUMENTS

| | | | |
|---|---|---|---|
| 1,090,106 | 3/1914 | Montine | 36/69 |
| 2,150,385 | 3/1939 | Maling | |
| 2,198,338 | 4/1940 | Greider | |
| 2,262,371 | 11/1941 | Reeves | |
| 2,409,813 | 10/1946 | Timson | |
| 2,509,821 | 5/1950 | Holstrom | 128/83.5 X |
| 2,614,340 | 10/1952 | Larkin | |
| 2,724,914 | 11/1955 | Wick | 36/37 |
| 3,006,083 | 10/1961 | Ogasawara | |
| 3,545,104 | 12/1970 | Laurie | 128/83.5 X |
| 3,555,706 | 1/1971 | Edmonds | |
| 3,566,487 | 3/1971 | Beightol | |
| 3,584,402 | 6/1971 | Silverman | 128/83.5 UX |
| 3,735,759 | 5/1973 | MacKay | 128/82 |
| 3,810,318 | 5/1974 | Epstein | |
| 3,820,254 | 6/1974 | Kopacsi | 36/110 |
| 3,847,147 | 11/1974 | Turner | 128/83.5 |
| 3,905,135 | 9/1975 | Debusk | |
| 4,178,703 | 12/1979 | Pols | 36/110 |

FOREIGN PATENT DOCUMENTS

| | | | |
|---|---|---|---|
| 670908 | 1/1939 | Fed. Rep. of Germany | 36/37 |
| 1280792 | 7/1972 | United Kingdom | 36/69 |

Primary Examiner—James Kee Chi
Attorney, Agent, or Firm—Z. T. Wobensmith, 2nd; Z. T. Wobensmith, III

[57] ABSTRACT

A removable shoe to be worn over a cast that extends over the foot of a person, which shoe provides protection to the cast and by use of a heel wedge preferably inserted in the shoe, and with an area below the main face of the wedge to accommodate the bottom of the cast, provides an improved walking action for the user.

4 Claims, 4 Drawing Figures

U.S. Patent  May 5, 1981  4,265,033
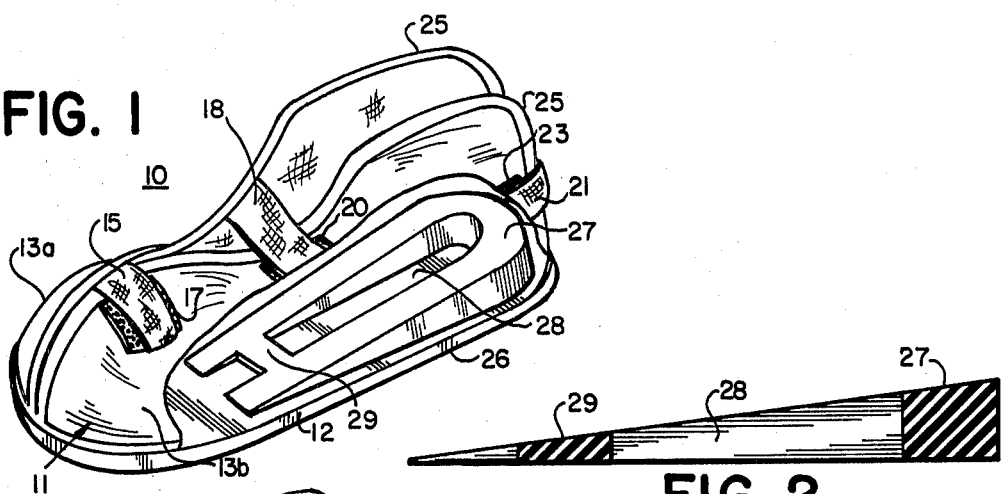
FIG. 1
FIG. 2
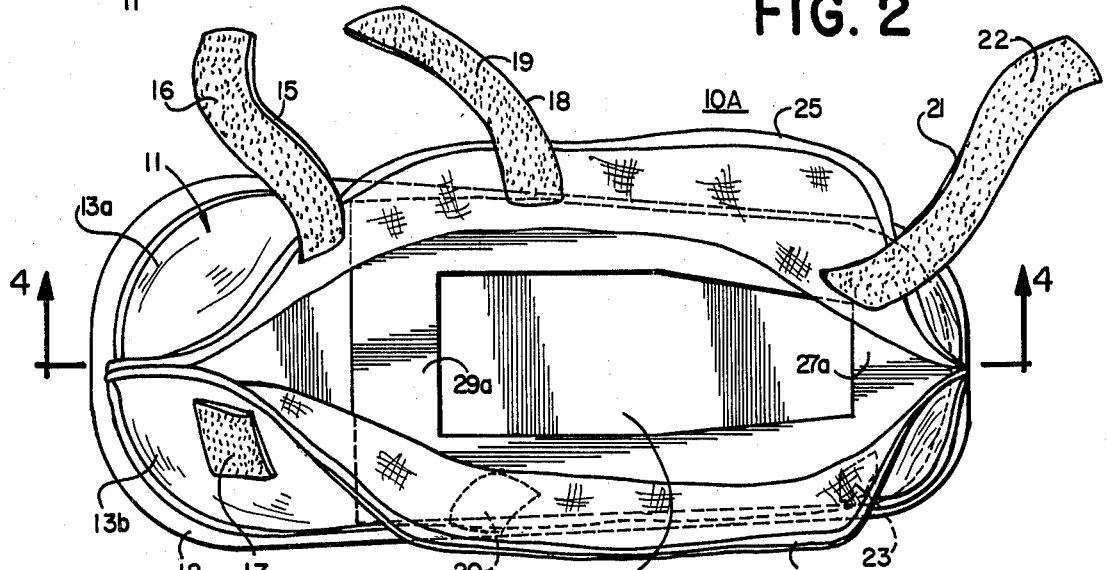
FIG. 3
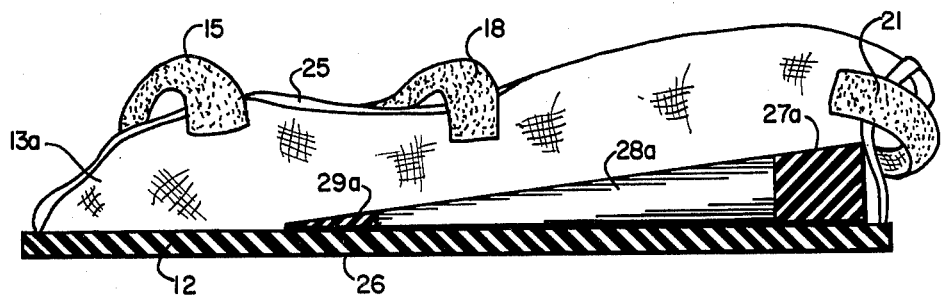
FIG. 4

SHOE TO BE WORN OVER CAST

BACKGROUND OF THE INVENTION

1. Field of the Invention

This invention relates to a removable shoe to be worn over a cast.

2. Description of the Prior Art

The modern medical view with persons who have to wear casts on a foot, or on the leg and foot, has been to encourage such person to exercise by walking consistent with the nature of the injury. Most casts in use are made of a plaster of paris material which is not highly resistant to moisture, and since many casts expose the toes and sometimes a portion of the heel to the elements the cast can easily deteriorate. A shoe that can be worn over the cast for protection and cast support is most desirable and until my invention no wholly satisfactory shoe has been available. Such a shoe should be easy to put on and take off and should assist the wearer in walking.

Shoes have been provided for wearing over casts and one such example is shown in the U.S. Pat. to R. F. Larkin, No. 2,614,340 which shows a walking cast shoe which extends over the toes and rearwards about ⅔ the length of the foot, with the heel of the cast exposed and the weight of the cast supported on a yoke 6 which contacts the ground outside the shoe thereby transmitting the ground contact shock directly to the cast, which in addition is not supported along the length of its bottom.

Various shoe constructions have been proposed which utilize a wedge type of construction for the sole and heel such as shown in the U.S. Pat. to Edmonds, No. 3,555,706 which shows athletic footwear, particularly basketball shoes, which includes an outer flat bottom sole 2 and an inner sole 3 of wedge shape but which shoe is not suitable for use with a cast.

Another example of footwear with wedge construction is shown in the U.S. Pat. to Maling, No. 2,150,385, which illustrates a shoe construction having a built up heel inside of the shoe, which built up heel is composed of resilient materials but is not suitable for a cast shoe.

Another example of footwear with an inner heel wedge inside the shoe is illustrated in the U.S. Pat. to Reeves, No. 2,262,371 which shows a heel wedge member 10 inside a shoe which is shaped to conform to the rear half of the bottom of a shoe but it is not suitable for a cast shoe.

Another example of wedge construction footwear is shown in the U.S. Pat. to Ogasawara, No. 3,006,083, which illustrates a ladies wedge style shoe which includes a wedge under the rear half of the foot which extends forward to the arch but is not suitable for use with a cast.

Another example of the wedge type of shoe construction is shown in the U.S. Pat. to Epstein, No. 3,810,318, which illustrates a shoe to aid children to learn to walk and which has an inner sole with extension and raised rear portion which extends about one half the length of the sole but which is not suited for a cast shoe.

Greider, in U.S. Pat. No. 2,198,338 shows a heel wedge for shoes which is not intended or suitable for a cast shoe.

Timson, in U.S. Pat. No. 2,409,813 shows a reversible shoe with a heel wedge which is not suitable for a cast shoe.

Debusk, U.S. Pat. No. 3,905,135, and Beightol, U.S. Pat. No. 3,566,487, show cast shoes but these, like the patents discussed above, are incapable of accomplishing the purposes of the cast shoe of the present invention and specifically the ease of application and removal, the accommodation to foot casts and the aid to walking of the cast shoe of the present invention.

SUMMARY OF THE INVENTION

This invention relates to a readily removable shoe to be worn over a cast which includes a heel wedge which has provisions to accommodate the cast and which aids the wearer to walk.

The principal object of the invention is to provide a shoe to be worn over a cast which accomodates and provides complete support to the cast for walking and which affords a high degree of protection to the cast.

A further object of the invention is to provide a shoe to be worn over a cast which is readily removable.

A further object of the invention is to provide a shoe to be worn over a cast which is simple and inexpensive to construction but is sturdy and reliable in use.

A further object of the invention is to provide a shoe to be worn over which aids the wearer to walk.

Other objects and advantageous features of the invention will be apparent from the description and claims.

DESCRIPTION OF THE DRAWINGS

The nature and characteristic feautures of the invention will be more readily understood from the following description taken in connection with the accompanying drawings forming part hereof in which:

FIG. 1 is a perspective view of one embodiment of the cast shoe of the invention, part of the shoe being broken away to show the cast support;

FIG. 2 is a vertical central sectional view of the cast support of the cast shoe of FIG. 1;

FIG. 3 is a top plan view of another embodiment of the shoe of the invention and having a different internal cast support; and FIG. 4 is a vertical sectional view taken approximately on the line 4-4 of FIG. 3.

It should, of course, be understood that the description and drawings herein are illustrative merely and various modifications and changes can be made in the structure disclosed without departing from the spirit of the invention.

Like numerals refer to like parts throughout the several views.

DESCRIPTION OF THE PREFERRED EMBODIMENTS

Referring now more particularly to the drawings and FIGS. 1 and 2 thereof, one embodiment of cast shoe 10 in accordance with the invention is illustrated. The shoe 10 consists of an upper 11 and a sole 12 attached to the upper 11 in any desired manner. The upper 11 is shown as being of split construction and is split into side halves 13a and 13b which respectively are disposed on either side of the cast. The upper halves 13a and 13b are joined to the sole 12 along its outer margin by a line of stitching (not shown) or by cementing and detachably secured together at the toe by a strap 15 secured to upper half 13a with a strip 16 of thistle cloth on one side of well known type, such as "Velcro", and which is shown as engaged with a complementary strip 17 of thistle cloth on the upper half 13b.

A second strap 18 is provided contiguous to the ankle and attached to upper half 13a with a strip 19 of thistle cloth on one side which is shown as engaged with a complemental strip 20 of thistle cloth on upper half 13b.

A third strap 21 is provided which extends around the rear of the cast at the rear of the ankle with a strip 22 of thistle cloth on one side for engagement with a complemental strip 23 of thistle cloth on the upper half 13b.

The upper halves 13a and 13b along their free edge may be provided with strips of cloth edging 25, and can be fabricated of any suitable type of reinforced material such as a vinyl backed cloth of well known type.

The sole 12 is fastened to the upper 11 in any suitable manner such as lines of stitching (not shown) and/or a film of adhesive of well known type. The sole 12 is preferably formed of a resilient relatively stiff spongy material and has a flat bottom surface 26 which may have a non-slip pattern thereon (not shown) of well known type.

An inner cast supporting heel wedge 27, of relatively stiff material is preferably secured by an adhesive to the top face of the sole 12. The wedge 27 is thicker at the rearmost portion of the heel, is preferably of a height of the order of one inch, and tapers down to a knife like edge terminating about two thirds the length of the sole 12 from the rear thereof. The heel wedge 27 preferably has a central cutout portion 28 to accommodate the transversely curved portion on the exterior of the cast which is more pronounced below the heel of the wearer. A cross brace 29 can be provided to prevent spreading of the wedge 27 when the weight of the wearer is applied on the wedge 27.

Referring now more particularly to FIGS. 3 and 4, another embodiment of shoe 10a is illustrated which includes an upper 11 and a sole 12. The upper 11 is formed of two side halves 13a and 13b which are joined to the sole 12 in any desired manner such as lines of stitching (not shown) or a film of adhesive of well known type.

The halves 13a and 13b of the upper 11 are provided with straps 15, 18 and 21 with strips of thistle cloth 17, 19 and 22 as in FIGS. 1 and 2 for respective engagement with complemental strips 17, 20 and 23.

The cast supporting heel wedge 27a of FIGS. 3 and 4 is similar to that of FIGS. 1 and 2 but the cross brace 29a is shown at the front thereof and bounding the cut out 28a.

When it is desired to use the cast shoe 10 or 10a the straps 15, 18 and 21 are detached from the strips 17, 19 and 22 and the foot with the cast thereon is inserted into the shoe, and the straps 15, 18 and 21 are attached to the respective strips 17, 19 and 22 with the desired degree of tightness to maintain the cast shoe in place.

The central cutout portions 28 and 28a receive the lower curved portion of the cast and prevent sidewise tilting of the cast with respect to the cast shoe.

The cast shoe is firmly held in place on the cast, provides protection of the cast against dirt and mud, the rise of the wedge to the rear tending to tilt the cast forwardly and aid the wearer in walking.

The cast shoe can be quickly and easily removed by detaching the straps 15, 18 and 21.

I claim:
1. A shoe to be worn over a cast which comprises
an upper which is adapted to fit around the lower portion of a cast and which has a toe and heel portion, the upper including
a pair of side halves detachably secured around the cast by a plurality of straps,
a sole having a toe and heel portion with a flat bottom surface and having said side halves joined to the sole along its outer margin,
said upper side halves meeting at the front and rear of the sole for enclosing the cast,
a continuously forwardly tapered cast supporting heel wedge within said upper and higher at the rear thereof and extending forwardly from the rear of the upper a distance of the order of two thirds of the length of the sole from the rear,
said wedge between its side margins having a central longitudinally extending cutout portion for the reception of the transversely curved bottom of the cast.
2. A shoe to be worn over a cast as defined in claim 1 in which
said wedge has a cross bracing portion rearwardly of its front edge.
3. A shoe to be worn over a cast as defined in claim 1 in which
said straps are attached to one of said upper halves, strips of thistle cloth are attached to said straps, and strips of complemental thistle cloth are attached to said other of said halves.
4. A shoe to be worn over a cast as defined in claim 1 in which
one of said straps is contiguous to the toe,
another of said straps is forward of the ankle, and
another of said straps is horizontally disposed around the heel.

* * * * *